(12) United States Patent
Takahara et al.

(10) Patent No.: US 10,278,329 B2
(45) Date of Patent: May 7, 2019

(54) GRAIN MANAGEMENT SYSTEM AND COMBINE

(71) Applicant: Kubota Corporation, Osaka-shi (JP)

(72) Inventors: Kazuhiro Takahara, Sakai (JP); Mao Ueda, Sakai (JP)

(73) Assignee: Kubota Corporation, Osaka (JP)

( * ) Notice: Subject to any disclaimer, the term of this patent is extended or adjusted under 35 U.S.C. 154(b) by 0 days.

(21) Appl. No.: 15/532,640

(22) PCT Filed: Dec. 25, 2015

(86) PCT No.: PCT/JP2015/086352
§ 371 (c)(1),
(2) Date: Jun. 2, 2017

(87) PCT Pub. No.: WO2016/147522
PCT Pub. Date: Sep. 22, 2016

(65) Prior Publication Data
US 2018/0153100 A1   Jun. 7, 2018

(30) Foreign Application Priority Data

Mar. 16, 2015 (JP) ................................. 2015-051973
Mar. 16, 2015 (JP) ................................. 2015-051974

(51) Int. Cl.
*A01D 41/12*   (2006.01)
*A01F 12/60*   (2006.01)
(Continued)

(52) U.S. Cl.
CPC ......... *A01D 41/1277* (2013.01); *A01D 41/12* (2013.01); *A01D 41/1208* (2013.01);
(Continued)

(58) Field of Classification Search
CPC .............. A01B 79/005; A01D 41/127; A01D 41/1275; A01D 41/12; A01D 41/1208;
(Continued)

(56) References Cited

U.S. PATENT DOCUMENTS 9,870,654 B2 * 1/2018 Tanabe .................. G07C 5/008
9,974,233 B2 * 5/2018 Ueda ....................... A01F 12/60
(Continued)

FOREIGN PATENT DOCUMENTS

EP   2390833 A1   11/2011
JP   1153674 A    2/1999
(Continued)

*Primary Examiner* — Robert E Pezzuto
(74) *Attorney, Agent, or Firm* — The Webb Law Firm

(57) ABSTRACT

A grain management system includes a combine and a management server. The combine includes a grain measurer for outputting a measured value related to a component of harvested grains supplied to a grain tank, and a data transmitter for transmitting the measured value and field identification information for specifying the field to the management server via a communication line. The management server includes a receiver for receiving the field identification information and the measured value from the combine, a table manager for determining a measured value-grain component value table for deriving a grain component value using the measured value based on the field identification information, and a grain component value computer for obtaining the grain component value based on the measured value, using the measured value-grain component value table that is determined by the table manager.

16 Claims, 10 Drawing Sheets

(51) Int. Cl.
*A01D 41/127* (2006.01)
*G06Q 50/02* (2012.01)
*G01N 21/85* (2006.01)

(52) U.S. Cl.
CPC .............. *A01F 12/60* (2013.01); *G01N 21/85* (2013.01); *G06Q 50/02* (2013.01); *G01N 2021/8592* (2013.01)

(58) Field of Classification Search
CPC ............ A01D 41/1277; A01D 41/1272; A01D 41/1274; A01F 12/18; A01F 12/46; A01F 12/60; E02F 9/205; E02F 9/2054; E02F 9/2246; G01F 13/005; G01F 13/006; G01F 23/0076; G01F 23/0007; G01F 25/0061; G01N 21/85; G01N 33/10; G07C 5/008; G07C 5/0825; G06Q 50/02
USPC ........... 56/10.2 A–10.2 G, 10.2 R; 172/2–11; 460/6, 59; 701/2, 50
See application file for complete search history.

(56) References Cited

U.S. PATENT DOCUMENTS

| | | | |
|---|---|---|---|
| 2006/0046800 A1* | 3/2006 | Kaltenheuser | A01D 41/12 460/6 |
| 2009/0325658 A1* | 12/2009 | Phelan | A01D 41/1275 460/6 |
| 2011/0290873 A1 | 12/2011 | Nishiguchi et al. | |
| 2012/0197465 A1* | 8/2012 | Gotou | E02F 9/205 701/2 |
| 2012/0253611 A1* | 10/2012 | Zielke | A01D 41/127 701/50 |
| 2014/0262548 A1* | 9/2014 | Acheson | G01G 11/003 177/1 |
| 2014/0274225 A1* | 9/2014 | Lacatus | H04W 24/08 455/574 |
| 2015/0242799 A1 | 8/2015 | Seki et al. | |
| 2015/0243114 A1 | 8/2015 | Tanabe et al. | |
| 2016/0029559 A1 | 2/2016 | Inoue et al. | |
| 2016/0066507 A1* | 3/2016 | Inoue | A01B 79/005 460/59 |
| 2016/0086032 A1* | 3/2016 | Pickett | G06F 17/40 382/110 |
| 2016/0330906 A1* | 11/2016 | Acheson | A01D 41/127 |

FOREIGN PATENT DOCUMENTS

| | | |
|---|---|---|
| JP | 200681487 A | 3/2006 |
| JP | 200681488 A | 3/2006 |
| JP | 201467308 A | 4/2014 |
| JP | 201467309 A | 4/2014 |
| JP | 2014187944 A | 10/2014 |
| JP | 2014194653 A | 10/2014 |

* cited by examiner

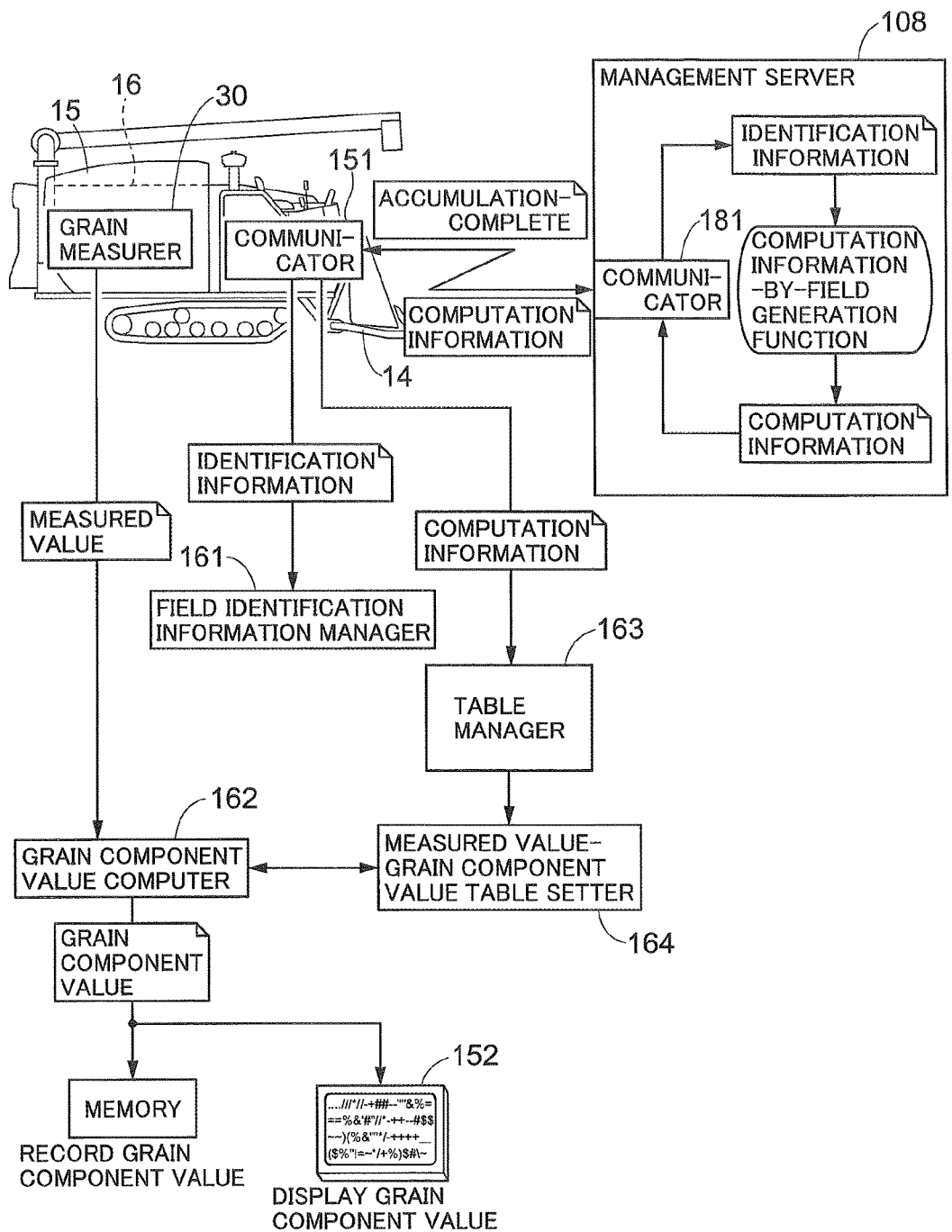

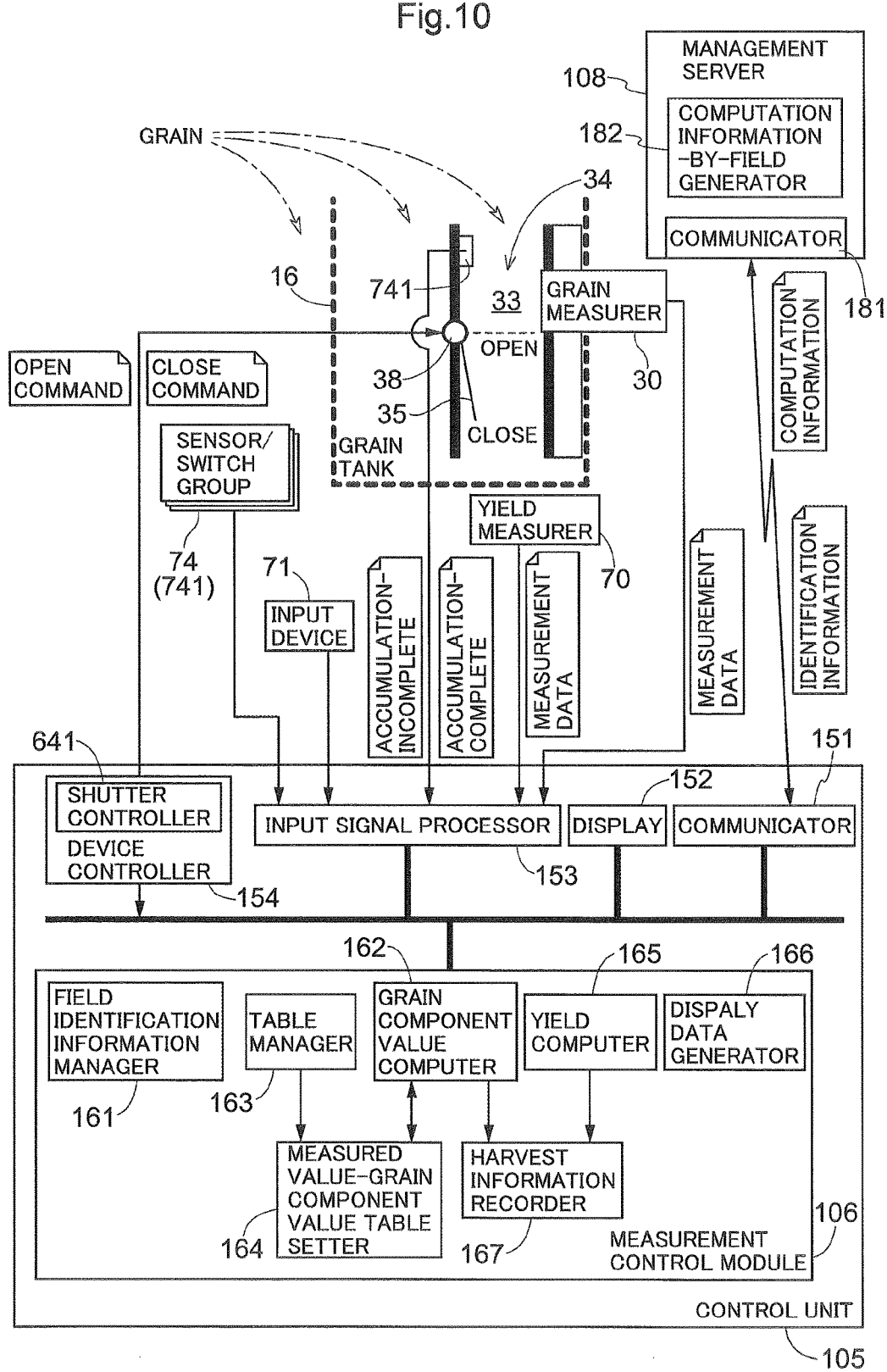

GRAIN MANAGEMENT SYSTEM AND COMBINE

CROSS-REFERENCE TO RELATED APPLICATIONS

This application is the U.S. national phase of International Application No. PCT/JP2015/086352 filed Dec. 25, 2015, and claims priority to Japanese Patent Application Nos. 2015-051973 and 2016-051974, both filed Mar. 16, 2015, the disclosures of which are hereby incorporated in their entirety by reference.

TECHNICAL FIELD

The present invention relates to a combine for reaping culms in a field while traveling, and accumulating, in a grain tank, grains obtained by threshing reaped culms, and to a grain management system for managing the quality of grains harvested by the combine.

BACKGROUND ART

A combine is known from Patent Document 1 that is provided, within a grain tank, with a moisture sensor for crushing grains flowing from a grain supply opening that leads to the grain tank, between rotating electrode rollers, and detecting an electrical resistance value of the grains in a crushed state. A grain moisture content measuring means for measuring the grain moisture content based on this electrical resistance value is provided in a control apparatus. This grain moisture content measuring means computes the grain moisture content based on the electrical resistance value from the moisture sensor, using a given computing equation for conversion into grain moisture content, and an LUT (look-up table). Specifically, the computing equation for conversion into grain moisture content, which is called a working curve, and the LUT are registered in advance for each type and breed of crop to be harvested, in a ROM.

Patent Document 2 discloses an agricultural management system that receives, from a combine, harvest position data, which indicates a harvest work position, as farmland information, harvest amount data, which indicates the harvest amount of farm produce harvested in a farmland, as farm produce information, and quality data, which indicates the quality thereof, and sends agricultural evaluation data to a user by performing agricultural evaluation on the farmland based on the farmland information and the farm produce information.

PRIOR ART DOCUMENTS

Patent Documents

Patent Document 1: JP 2006-081488A
Patent Document 2: JP 2014-067308A

DISCLOSURE OF THE INVENTION

Problem to be Solved by the Invention

It is possible for the agricultural management system according to Patent Document 2 to realize accurate farming management in units of fields. To realize this, accurate quality data is required. The grain moisture content measuring means provided in the combine according to Patent Document 1 uses a working curve (a table for deriving a grain moisture content value from a measured value) that is registered in advance in the ROM in the control apparatus. However, even in the case of the same type and breed of crop, the relationship between measured values and grain component values (which include the grain moisture content value) differs depending on the region or the year. Furthermore, in the case where, regarding the measured value based on which the grain moisture content is derived, a measurement method is employed in which the relationship between a measured value such as a spectrometric value, rather than the electrical resistance value, and the grain component value is highly accurate, if a pre-registered working curve simply continues to be used for each type and breed of crop, grain components cannot be satisfactorily calculated, which is inconvenient.

In view of the foregoing situation, there is a need for an agricultural management system in which agricultural evaluation is performed using more accurate grain component values, and that, as a result, can realize reliable farming management. Also, there is a need for a combine that is capable of obtaining more accurate grain component values during harvest.

Means for Solving Problem

A grain management system according to the present invention includes: a combine for reaping culms in a field while traveling, and accumulating, in a grain tank, grains obtained by threshing reaped culms; and a management server for managing quality of the grains harvested by the combine. The combine includes: a grain measurer for outputting a measured value related to a component of the grains supplied to the grain tank; and a data transmitter for transmitting the measured value and field identification information for specifying the field to the management server via a communication line. The management server includes: a receiver for receiving the field identification information and the measured value from the combine; a table manager for determining a measured value-grain component value table for deriving a grain component value using the measured value based on the field identification information; and a grain component value computer for obtaining the grain component value based on the measured value using the measured value-grain component value table that is determined by the table manager.

With this configuration, the measured value related to the grain component output from the grain measurer in the combine is sent, together with the field identification information for specifying the field in which the grains have been harvested, from the combine to the management server. In the management server, an optimum measured value-grain component value table for the grains harvested in this field is determined based on the field identification information, and the grain component value is derived from the measured value using this measured value-grain component value table. Thus, the latest measured value-grain component value table in which the harvest region, harvest year, and the like are given consideration, i.e. an optimum measured value-grain component value table for the grains harvested in the field that is currently subjected to harvest work, is used. Accordingly, an accurate grain component value is obtained, and reliable farming management can be realized.

In a preferable embodiment of the present invention, the management server includes a field database that records a type and/or a breed of grain harvested in each field so as to be able to be read out, based on the field identification information, and the table manager determines an optimum measured value-grain component value table based on the type and/or breed of grain read out from the field database. With this configuration, the optimum measured value-grain component value table for deriving the component value of those grains from the measured value is determined based on the type and/or breed of grain that is read out from the field database. In this regard, it is preferable that, in order to determine an optimum measured value-grain component value table for grains that are to be actually harvested, the management server is configured to be able to acquire the type and breed of grain to be harvested, the region and season, the quality status of grains harvested in a nearby field, and the like, based on the field identification information regarding the field that is sent from the combine. Thus, it is possible to suppress errors in the grain component value due to a difference in the type of grain, or a difference in the breed of grain.

In a preferable embodiment of the present invention, the management server includes a table storage for storing, in an extractable manner, a plurality of the measured value-grain component value tables associated with a type and/or breed of harvested grain, and the measured value-grain component value table extracted from the table storage using, as a search condition, a type and/or a breed of grain read out from the field database is determined as the optimum measured value-grain component value table. With this configuration, the plurality of measured value-grain component value tables with different relationships between the measured value and the grain component value are stored in an extractable manner in the combine, the measured value-grain component value tables being created while giving consideration to each type and breed of crop to be harvested, as well as variation among regions and years, and the like. The management server installed in a central management center or the like can create the search condition for extracting the optimum measured value-grain component value table for grains that are to be actually harvested by the combine, using the type and breed of grain to be harvested, and preferably the region and season, and more preferably the quality state of grain harvested in a nearby field, and the like, which are determined based on the field identification information regarding the field that is sent from a large number of combines. By using the optimum measured value-grain component value table that is set using this search condition by the table manager, the grain component value computer can calculate an accurate grain component value based on the measured value that is sent from the combine.

In a preferable embodiment of the present invention, the management server holds a reference measured value-grain component value table to serve as a reference of the measured value-grain component value table, and the table manager determines the optimum measured value-grain component value table by correcting the reference measured value-grain component value table based on the type and/or breed of grain read out from the field database. In this embodiment, only the reference measured value-grain component value table is prepared. The type and/or breed of the grain for which computation is to be performed is read out based on the field identification information regarding the field that is sent from the combine. Furthermore, an optimum measured value-grain component value table is created by correcting the reference measured value-grain component value table based on the type and/or breed of those grains, and is used for computing the grain component value.

The management server is built so as to be shared between many farmers. For this reason, to support farm planning for each farm, it is important that the grain component value of grains harvested in each field can be downloaded from the management server to each farm. For this reason, in a preferable embodiment of the present invention, the management server comprises a transmitter for transmitting, to the combine, the grain component value obtained by the grain component value computer. In this regard, if the combines includes a receiver for receiving the grain component value transmitted from the transmitter in the management server, and a display capable of displaying the grain component value, an operator who is carrying out harvest work using the combine can check the grain component value in real-time or in the middle of work, which is convenient.

If the operator of the combine is interested in farming management for the field in which harvest work is being carried out, it is convenient if the operator can check the grain components or the like of the grains that are being harvested, in real-time or in the middle of work. For this reason, in a preferable embodiment of the present invention, the combines includes a receiver for receiving the grain component value transmitted from the transmitter in the management server, and a display capable of displaying the grain component value.

With the combine according to the present invention, an accurate grain component value can be obtained based on the measured value from the grain measurer, as mentioned above. For this reason, it is preferable that the grain measurer also performs detailed grain measurement using an accurate measurement method, in units of minute parcels of the field, rather than in units of fields. For this reason, a preferable embodiment of the present invention employs a configuration in which a temporary accumulation chamber for receiving at least some of the grains supplied to the grain tank is provided, the grain measurer outputs the measured value based on spectrometry performed on light with which the grains temporarily accumulated in the temporary accumulation chamber are irradiated, and the grain component value computer obtains at least a moisture content based on the measured value. With this configuration, harvested grains sequentially accumulate in the temporary accumulation chamber, and the content of a grain component thereof, or more particularly the moisture content, which is highly associated with taste, is accurately obtained through spectrometry. Thus, farming management in units of minute parcels of the field can be performed.

If the protein component, which is an important nutrient component of grains, can be measured together with the moisture content, it is convenient in terms of farming management. For this reason, a preferable embodiment of the present invention is configured such that the grain component value computer derives a component value of protein from the measured value.

A combine according to the present invention for reaping culms in a field while traveling, and accumulating, in a grain tank, grains obtained by threshing reaped culms includes: a field identification information manager for managing field identification information for specifying the field; a grain measurer for outputting a measured value related to a component of the grains supplied to the grain tank; a communicator for transmitting the field identification information to the management server via a communication line, and receiving, from the management server, computation information for the field specified based on the field identification information; a table manager for determining, using the computation information, an optimum measured value-grain component value table for deriving, from the measured value, a grain component value indicating a component of grains harvested in the field; and a grain component value computer for obtaining the grain component value based on the measured value using the measured value-grain component value table that is determined by the table manager.

With this configuration, the measured value-grain component value table for deriving the grain component value from the measured value related to a grain component output from the grain measurer is determined using the computation information that is received from the management server via the communication line. In this regard, the management server, which has received, from the combine, the field identification information regarding the field subjected to harvest, transmits, to the combine, the computation information for determining the optimum measured value-grain component value table for deriving the grain component value of the grains to be harvested in this field based on the field identification information. Thus, a reliable grain component value can be obtained using the latest measured value-grain component value table in which the harvest region, the harvest year, and the like are given consideration, i.e. an optimum measured value-grain component value table for the grains harvested in the field that is currently being subjected to harvest work.

In a preferable embodiment of the present invention, a table storage for storing a plurality of the measured value-grain component value tables for deriving the grain component value from the measured value is provided, and the table manager determines, as the optimum measured value-grain component value table, the measured value-grain component value table extracted from the table storage using the computation information as a search condition. Note that a measured value-grain component value table stored in the table storage is added or updated, giving consideration to environmental conditions such as the weather in the harvest region, breeding, or the like. Thus, a large number of measured value-grain component value tables are stored in an extractable manner, the tables being created by giving consideration to the type and breed of the crop to be harvested, as well as variation among regions or years, and the like, and having slightly different relationships (which are also called measurement lines) between the measured value and the grain component value. The management server installed in a central management center or the like creates the search condition for extracting an optimum measured value-grain component value table for grains that are to be actually harvested by the combine, using, as input parameters, the type and breed of harvested grain determined based on the field identification information regarding the field that is sent from the combine, the region and season, the state of the quality of harvested grains in the nearby field, and the like. The search condition is sent as computation information to the combine. Upon the combine receiving the search conditions from the management server, an optimum measured value-grain component value table for the grains to be harvested is set based on the search condition, and the grain component value computer can calculate an accurate grain component value using this optimum measured value-grain component value table.

In another embodiment of the present invention, a reference measured value-grain component value table to serve as a reference of the measured value-grain component value table is stored, and the table manager determines the optimum measured value-grain component value table by correcting, based on the computation information, the reference measured value-grain component value table. In this embodiment, unlike the previous embodiment, the combine only has the reference measured value-grain component value table, instead of a plurality of measured value-grain component value tables. The combine corrects the reference measured value-grain component value table based on the computation information that the combine receives as a result of the field identification information regarding the field being sent to the management server, and creates an optimum measured value-grain component value table for the grains that are to be harvested. Accordingly, the computation information in this embodiment is correction information for creating an optimum measured value-grain component value table based on the reference measured value-grain component value table.

Note that, in the above-described two embodiments, the computation information that is sent in accordance with the field identification information regarding the field from the management server is used so that the combine uses an optimum measured value-grain component value table. The simplest information of this computation information is the type and/or breed of the grain to be harvested in the field. With this configuration, the management server acquires, from the field identification information regarding the field, the type and/or breed of the grain to be harvested in this field at the current time point. As a result, it is possible to appropriately notify the combine performing harvest work in fields, of the computation information, which is the type and/or breed of the harvested grain. Thus, it is possible to avoid an error in calculating the grain component value due to a difference between the type or breed of grain in the set measured value-grain component value table and the type or breed of grain that is actually being harvested.

A conventional combine or the like does not include a function of extracting an optimum measured value-grain component value table from a plurality of measured value-grain component value tables, or a function of correcting a reference measured value-grain component value table to create an optimum measured value-grain component value table. In such a case, an embodiment in which the computation information is the optimum measured value-grain component value table for deriving the grain component value from the measured value is convenient. The management server selects or creates an optimum measured value-grain component value table based on the field identification information regarding the field that is sent from the combine. As a result of the table manager receiving this measured value-grain component value table from the management server and setting the received table, the grain component value computer can obtain an accurate grain component value based on the measured value.

As mentioned above, the combine according to the present invention can obtain an accurate grain component value based on the measured value of the grain measurer. For this reason, it is preferable that the grain measurer also performs detailed grain measurement using an accurate measurement method, in units of minute parcels of the field, rather than in units of fields. For this reason, a preferable embodiment of the present invention employs a configuration in which a temporary accumulation chamber for receiving at least some of the grains supplied to the grain tank is provided, the grain measurer outputs the measured value based on spectrometry performed on light with which the grains temporarily accumulated in the temporary accumulation chamber are irradiated, and the grain component value computer obtains at least a moisture content based on the measured value. With this configuration, harvested grains sequentially accumulate in the temporary accumulation chamber, and the content of a grain component thereof, or more particularly the moisture content, which is highly associated with taste, is accurately obtained through spectrometry. Thus, farming management in units of minute parcels of the field can be performed.

If the protein component, which is an important nutrient component of grains, can be measured together with the moisture content, it is convenient in terms of farming management. For this reason, a preferable embodiment of the present invention is configured such that the grain component value computer derives a component value of protein from the measured value.

The combine according to the present invention can obtain the grain component value in units of minute parcels of the field during harvest. Accordingly, in the case where the combine is being driven by an operator who is familiar with farm management, it is convenient if this grain component value can be checked in real-time or during work. For this reason, in a preferable embodiment of the present invention, a display capable of displaying the grain component value is provided.

Other features and configurations, as well as advantageous effects achieved thereby will become apparent by reading the following description with reference to the attached drawings.

BRIEF DESCRIPTION OF THE DRAWINGS

FIG. 9 is a schematic diagram illustrating a second embodiment (which also applies to FIG. 10), and shows a basic configuration for deriving an accurate grain component value based on a measured value for harvested grains.

FIG. 10 is a functional block diagram showing one example of a measurement control system that is built in a combine.

BEST MODE FOR CARRYING OUT THE INVENTION

First Embodiment

Hereinafter, the first embodiment will be described with reference to FIGS. 1 to 8.

Figure 1:
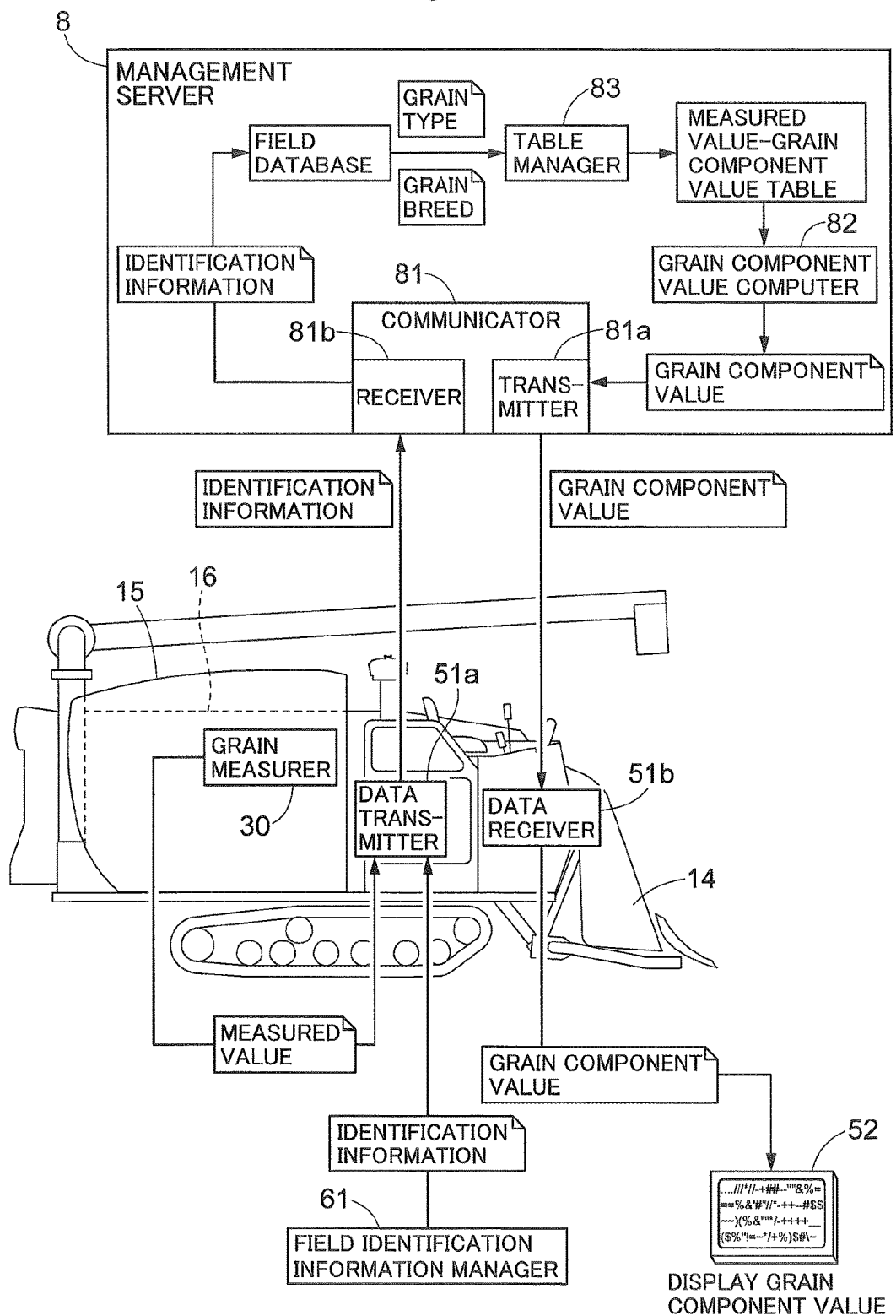
FIG. 1 is a schematic diagram illustrating a first embodiment (which also applies to FIGS. 2 to 8), and shows a basic configuration for obtaining an accurate grain component value based on a measured value that is sent from a combine.

Before describing a specific configuration of a grain management system that serves as the first embodiment of the present invention, a description will be given, using FIG. 1, of a basic configuration of the grain management system that calculates a grain component value in cooperation with a management server when the combine harvests grains. Here, the combine reaps culms in a field using a reaper 14 while traveling, and grains are removed from the reaped culms by a threshing apparatus 15. Grains are supplied from the threshing apparatus 15 to a grain tank 16 by a grain conveyance mechanism. The combine includes a grain measurer 30 for outputting a measured value related to a component of the grains supplied to the grain tank 16, and a field identification information manager 61 for managing field identification information for specifying a field. In the grain measurer 30, at least some of the grains are taken into a grain supply passage extending from the threshing apparatus 15 to the grain tank 16, and measurement regarding grain components is performed. The field identification information manager 61 generates field identification information for specifying the field in which harvest work is to be performed from now, through manual input performed by an operator using an input device such as a touch panel, automatic input using a beacon or the like that is installed in the field, matching between a field map and GPS positioning data, or the like. The combine also includes a data transmitter 51a and a data receiver 51b that can be connected, in a data-exchangeable manner, to a communicator 81 (which includes a transmitter 81a and a receiver 81b) in the management server 8 through a data communication network, such as a wireless public line or the Internet. If this combine is provided with a display 52, such as a liquid-crystal display, that is capable of displaying the grain component value when harvesting grains that is sent from the management server 8, the operator can check the grain component value during harvest work, which is convenient.

The management server 8 includes a grain component value computer 82 for obtaining a grain component based on the measured value sent from the combine. Note that, in the case where the grain to be harvested is rice or wheat, the grain components that affect the taste thereof are moisture and the protein. Accordingly, here, the grain components obtained by the grain component value computer 82 are moisture and protein. When obtaining the grain component values, the grain component value computer 82 uses a function or a table in which the measured value that is output from the grain measurer 30 in the combine and is sent to the management server 8 is an input value, and a specific grain component value is an output value. Here, this function or table (a simple one is also called a measurement line) will be referred to as a measured value-grain component value table, which is for deriving the grain component value from the measured value. The relationship between the measured value and the grain component value differs depending on the type, state, or the like of the grains that are to be measured. Accordingly, to obtain an accurate grain component value, an optimum measured value-grain component value table (measurement line) for the grains to be measured needs to be used. For this reason, the management server 8 includes a table manager 83 in order to determine an optimum measured value-grain component value table. The management server 8 receives the field identification information for specifying a field sent from the combine. The latest information regarding harvested grains, e.g. the type and/or breed of the grain, can be acquired from this field identification information. For example, if a field database, which records the type and/or breed of the grain to be harvested in each field so as to be able to be read out, based on the field identification information, is built in the management server 8, the table manager 83 can access the field database to read out the type and/or breed of the grain to be harvested in the field that is subjected to work. The table manager 83 can optimally generate or select a measured value-grain component value table based on the read type and/or breed of the grain. The grain component value computer 82 obtains the grain component value based on the measured value sent from the combine, using the optimum measured value-grain component value table that is determined by the table manager 83.

Two exemplary configurations will be described below, which are employed for the table manager 83 in order to determine the optimum measured value-grain component value table based on the type and/or breed of grain.
(1) A large number of measured value-grain component value tables are prepared in advance in the table manager 83. When an optimum measured value-grain component value table for the field specified based on field identification information is extracted from among these tables, an extraction condition is used that is created based on the type and/or breed of the grain to be harvested in the field specified based on the field identification information.
(2) Only a reference measured value-grain component value table to serve as a reference of the measured value-grain component value table is prepared in advance. An optimum measured value-grain component value table for the specified field is created by correcting the reference measured value-grain component value table. For example, a coefficient group (which includes the tilt of the measurement line, the amount of translation, and the like) for a function of obtaining the grain component value based on the measured value is determined based on the type and/or breed of the grain. Using this coefficient group, the optimum measured value-grain component value table is created based on the reference measured value-grain component value table.

Of course, (1) and (2) can also be combined.

As the grain measurer 30 for outputting the measured value related to a component of the grains supplied to the grain tank 16, an optical measurement apparatus can be employed that outputs a measured value based on spectrometry performed on light with which the grains are irradiated, the grains being temporarily accumulated in a temporary accumulation chamber for receiving at least some of the grains supplied to the grain tank 16. In this case, by repeating, during harvest work, calculation of the grain component while temporarily accumulating harvested grains, a grain component value per unit of travel distance, i.e. per minute parcel of a field, can be obtained. A distribution map of the grain component value in a specific field can be created based on this grain component value per minute parcel, which allows accurate farming management to be realized.

In the case where the crop to be harvested is rice or wheat, the grain components that affect the taste thereof are moisture and protein. For this reason, it is preferable that the grain measurer 30 can output measurement data on moisture and protein.

There is also a need for an operator of the combine to be able to check the grain component value of harvested grains during harvest work. For this reason, the grain component values (moisture and protein) obtained by the grain component value computer 82 in the management server 8 are transmitted to the combine. The grain component values are displayed on the display 52 such as a liquid-crystal display that is provided in the combine. The grain component values obtained by the grain component value computer 82 are also sent from the management server 8 to computers installed at farms and portable communication terminals carried by farmers.

Figure 2:
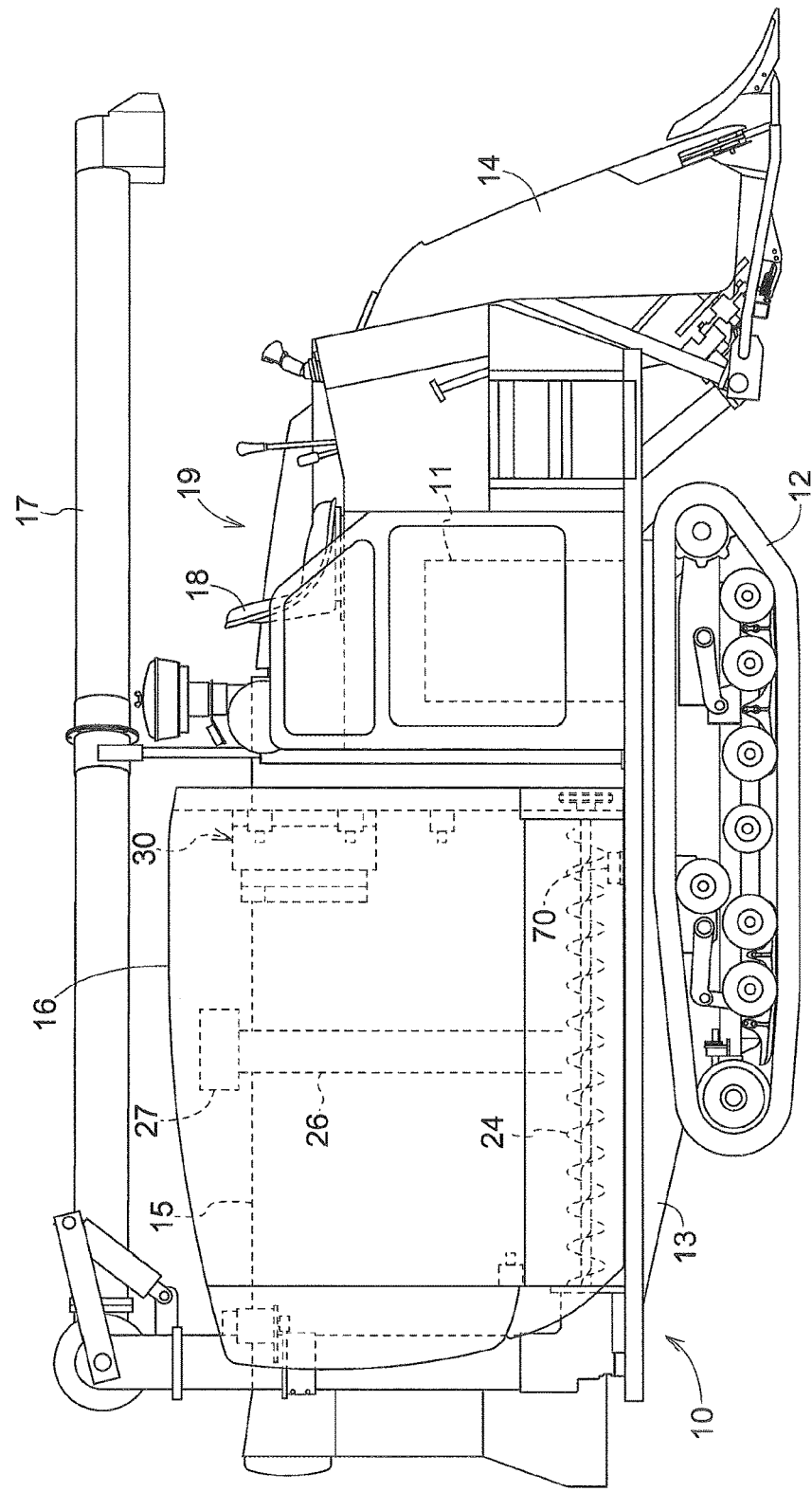
FIG. 2 is a side view showing an example of a combine that constitutes a grain management system according to the present invention.
Figure 3:
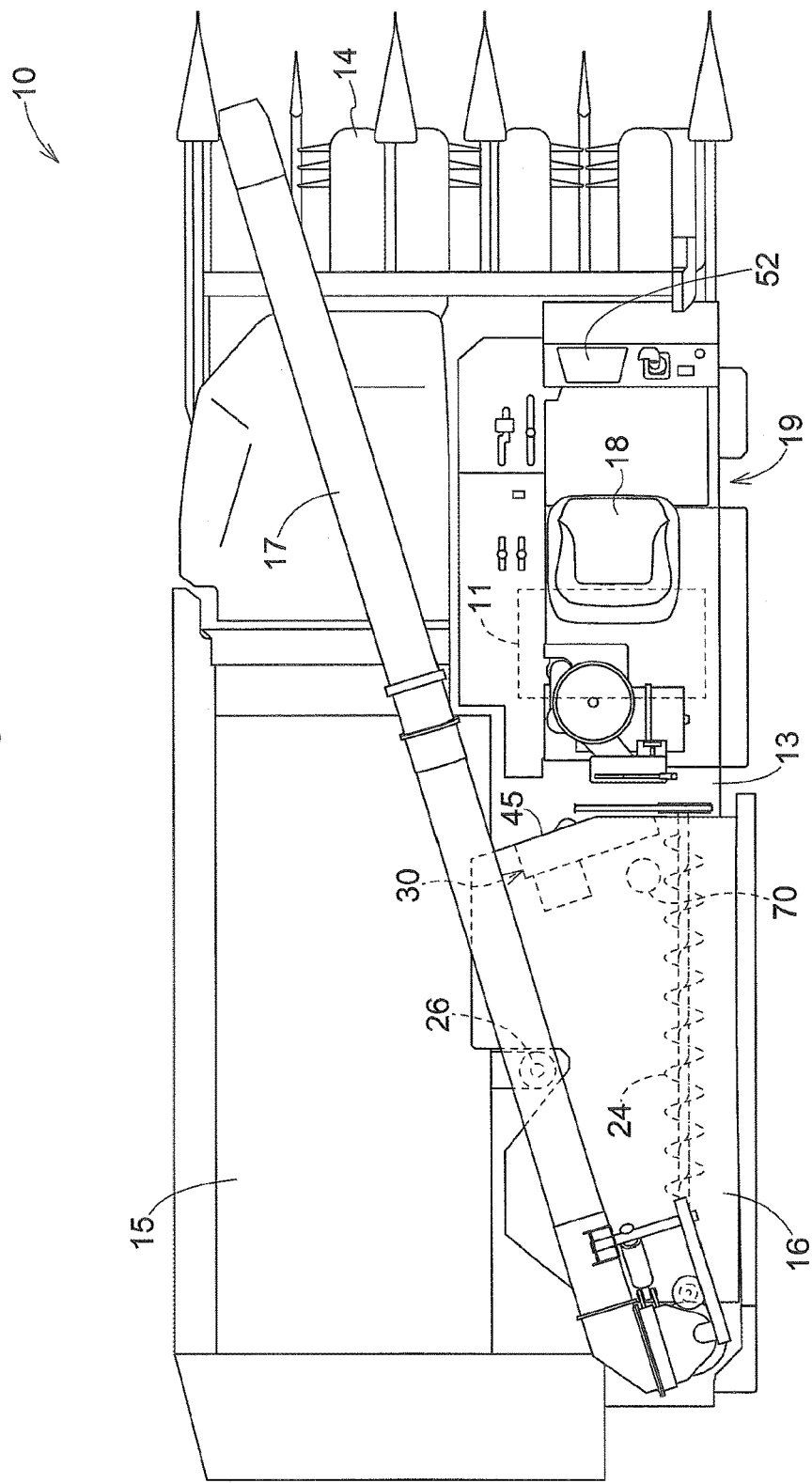
FIG. 3 is a plan view of the combine.

Next, a specific embodiment of the grain management system according to the present invention will be described using the drawings. FIG. 2 is a side view of a self-threshing combine of a crawler travel type. FIG. 3 is a plan view. This combine includes a traveling body 10, which is configured to be self-propelled by a pair of left and right crawler traveling apparatuses 12 that are driven by an engine 11. The combine includes a reaper 14 for reaping plant culms that is supported at a front portion of a machine body frame 13 of the traveling body 10, a threshing apparatus 15 for threshing reaped culms, a grain tank 16 for accumulating grains threshed by the threshing apparatus 15, an unloader 17, which is a grain discharge apparatus for discharging grains in the grain tank 16 to the outside, an operating/steering section 19 that is provided with an operator seat 18 on which an operator sits, and the like.

Figure 4:
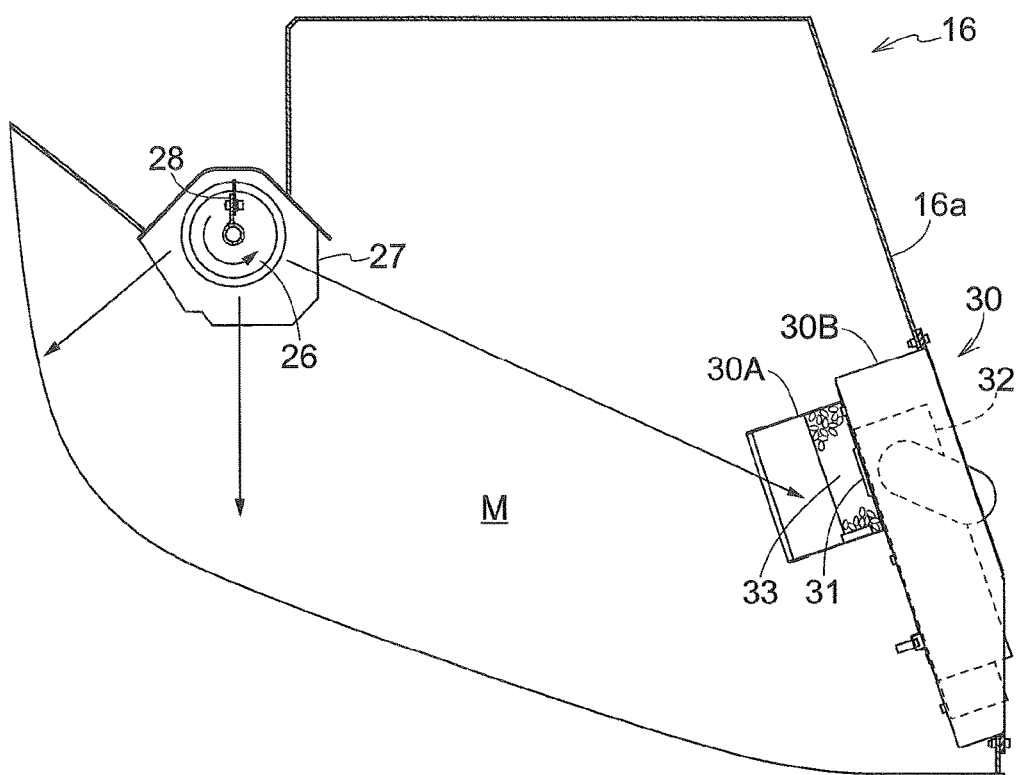
FIG. 4 is a traversal plan view showing a front portion of a grain tank that is mounted in the combine.

As shown in FIGS. 2 and 3, the grain tank 16 is arranged on the right side, relative to the threshing apparatus 15, of the machine body frame 13, and is located rearward of the engine 11. A lifting screw 26 is provided in a left side portion of the grain tank 16. The lifting screw 26 is arranged in a left portion, relative to the machine body, within the grain tank 16. The lifting screw 26 lifts grains conveyed from the threshing apparatus 15 up to an inlet port 27. As shown in FIG. 4, grains lifted up to the inlet port 27 are flung out from the inlet port 27 by a rotary blade 28, which is integrally provided with the lifting screw 26 and is driven to rotate counterclockwise. The grains then fly while being dispersed over a wide area in the grain tank 16, and fall down. Most of the grains supplied from the inlet port 27 are supplied to the internal space M of the grain tank 16. The grain measurer 30 for outputting a measured value related to a component of the grains is arranged in a front portion of the grain tank 16. This grain measurer 30 temporarily accumulates therein some of the grains supplied from the inlet port 27, irradiates the grains in an accumulated state with a light beam, and outputs the result of spectral measurement performed on a returned light beam.

As shown in FIGS. 2 and 3, a discharge auger 24, which is configured to discharge grains accumulated in the grain tank 16 to the outside and is oriented in a front-rear direction relative to the machine body, is provided at the bottom of the grain tank 16. The discharge auger 24 is operated with the driving force generated by the engine 11. Grains accumulated in the grain tank 16 are discharged from a rear portion of the grain tank 16 by the discharge auger 24, and are further discharged to the outside through the unloader 17.

As shown in FIGS. 2 and 3, a load cell, which is configured to measure the yield of grains in the grain tank 16 based on the weight of the grain tank 16, is provided as a yield measurer 70 at a position below the front portion of the grain tank 16.

Figure 5:
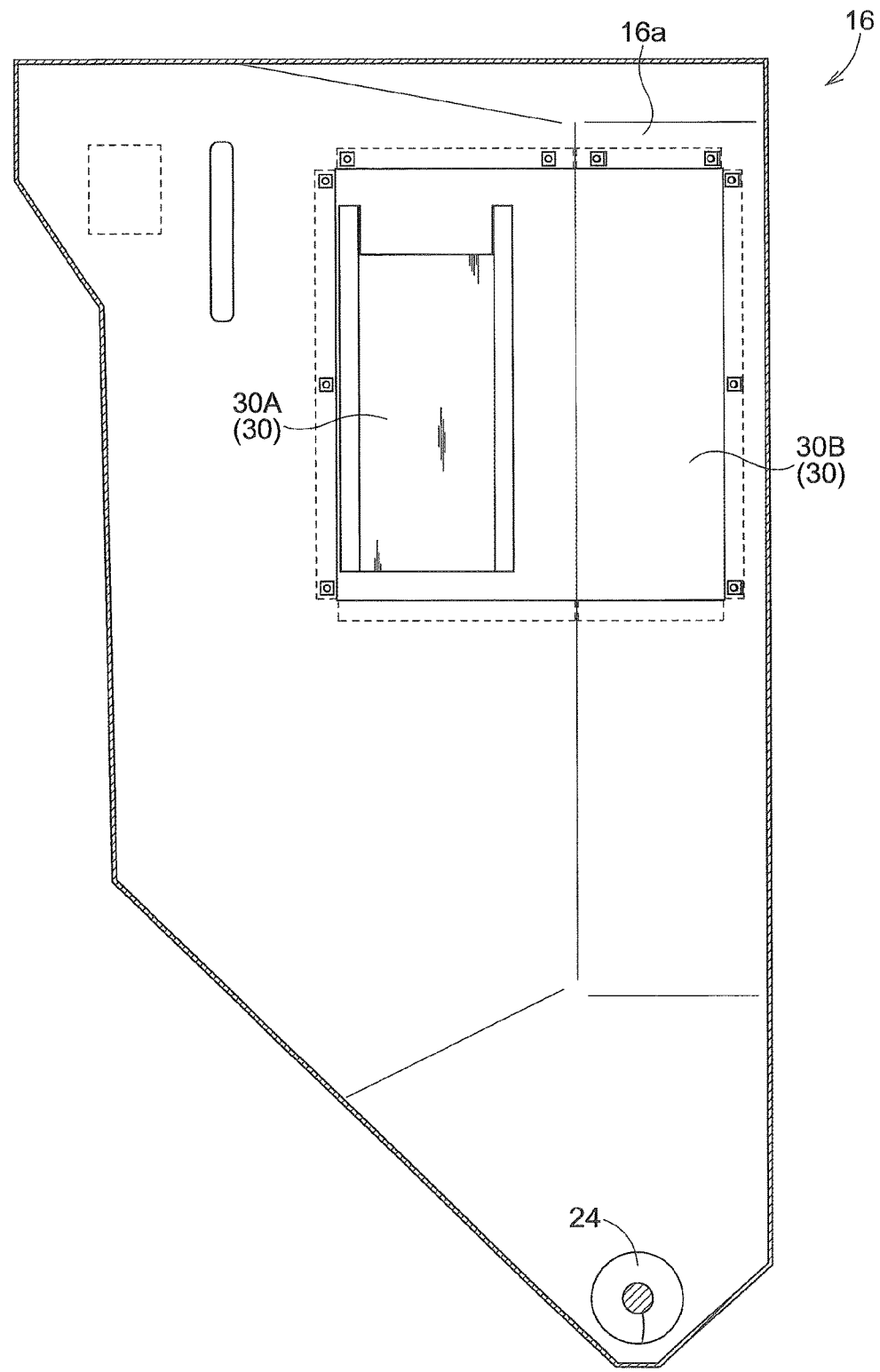
FIG. 5 is a schematic diagram showing the inside of the grain tank.
Figure 6:
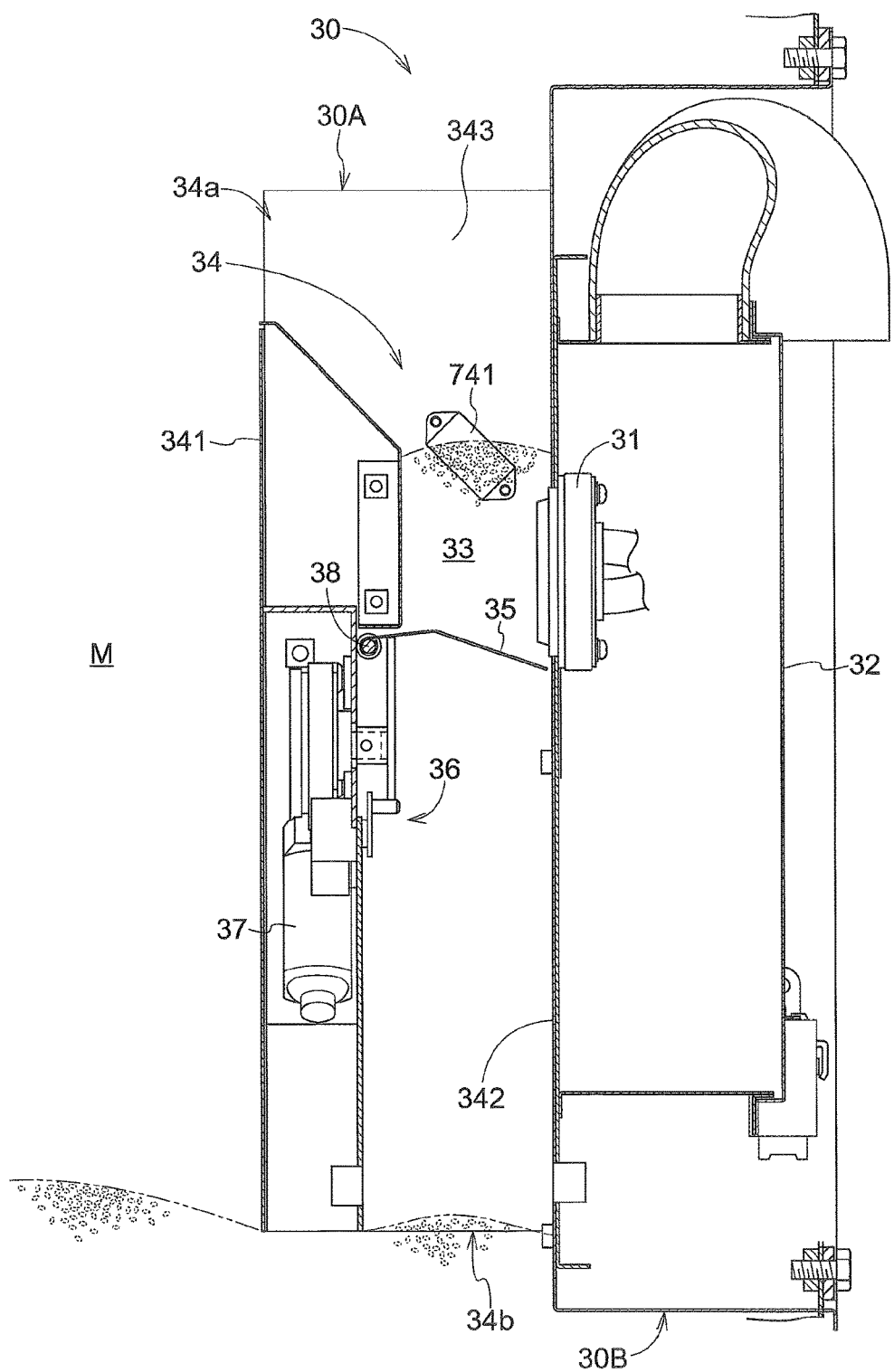
FIG. 6 is a longitudinal side view of a measurement unit at the time when an accumulation shutter, which is provided within a tubular-shaped body provided in the grain tank, is at a close position.
Figure 7:
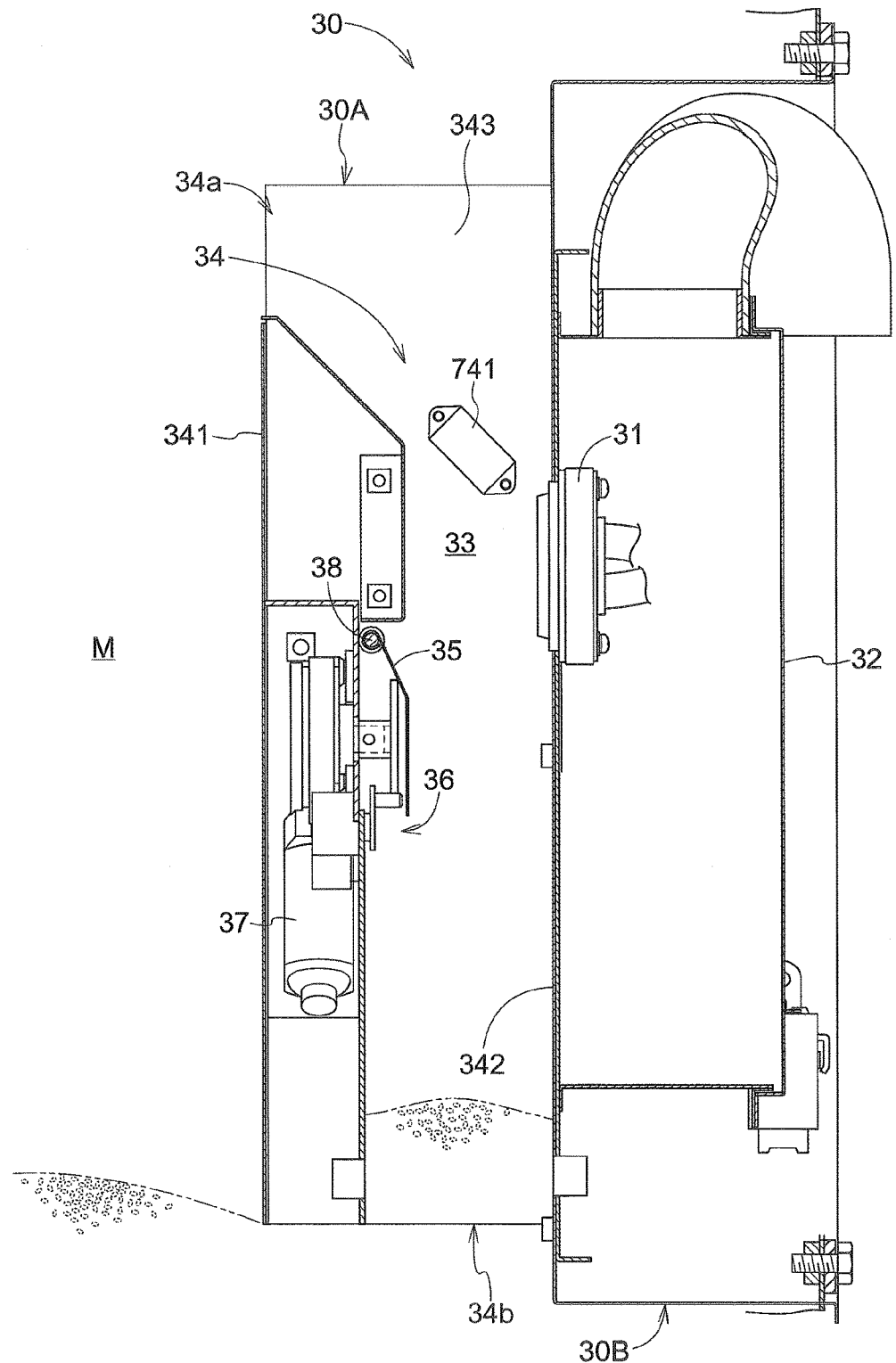
FIG. 7 is a longitudinal side view of the measurement unit at the time when the accumulation shutter is at an open position.

As shown in FIG. 5, the grain measurer 30 is fixed with screws to a front wall 16a of the grain tank 16 via rubber cushions. The grain measurer 30 is constituted by a measurement container 30A and a measurement unit 30B. As shown in FIGS. 6 and 7, the measurement unit 30B includes a box-shaped housing 32, which has a built-in optical probe 31 for acquiring measurement data on component values of moisture and protein of grains. The measurement container 30A includes a temporary accumulator 33 for temporarily accumulating grains on which grain component measurement using the optical probe 31 is to be performed.

The measurement container 30A is a tubular body having a rectangular cross section constituted by a first wall 341, which faces the internal space M of the grain tank 16, a pair of left and right side walls 343, and a second wall 342, which faces the measurement unit 30B. Note that, in this embodiment, the second wall 342 is shared in its vertical wall portion facing the internal space M of the housing 32. Of course, the second wall 342 may be individually provided. With this structure for the measurement container 30A, a vertically-extending grain passage 34 is created therein, and the temporary accumulator 33 is formed in the middle of the grain passage 34. The grain passage 34 has a take-in port 34a in an upper portion thereof for taking in grains, and a discharge port 34b in a lower portion thereof for discharging grains.

The temporary accumulator 33 is configured to temporarily accumulate some of the grains that are conveyed from the threshing apparatus 15 and flung out by the rotary blade 28 (see FIG. 4). The temporary accumulator 33 is configured to take in, from the take-in port 34a formed in the upper portion of the temporary accumulator 33, some of the grains conveyed from the threshing apparatus 15, temporarily accumulate these grains, and discharge the grains accumulated in the temporary accumulator 33 from the discharge port 34b formed in the lower portion of the temporary accumulator 33 toward the internal space M of the grain tank 16. In the upper portion of the temporary accumulator 33, an accumulation amount detector 741, which is constituted by a proximity sensor for detecting grains, is provided in the side wall 343 of the measurement container 30A. In the lower portion of the temporary accumulator 33, an accumulation shutter 35 for closing or opening the discharge port 34b is provided. The optical probe 31 for detecting the quality of grains accumulated in the temporary accumulator 33 faces the temporary accumulator 33.

The accumulation shutter 35 is configured to be plate-shaped and pivotable. The accumulation shutter 35 is switched between an accumulating close position at which the accumulation shutter 35 assumes a horizontal posture, and a discharging open position at which the accumulation shutter 35 assumes a downward vertical posture, by a switching mechanism 36, which is constituted by a cam or the like, as per the driving of a motor 37. The accumulation shutter 35 pivots around a horizontal support shaft 38, which intersects an open-close direction of the accumulation shutter 35. The support shaft 38 is supported by the first wall 341 of the measurement container 30A.

Figure 8:
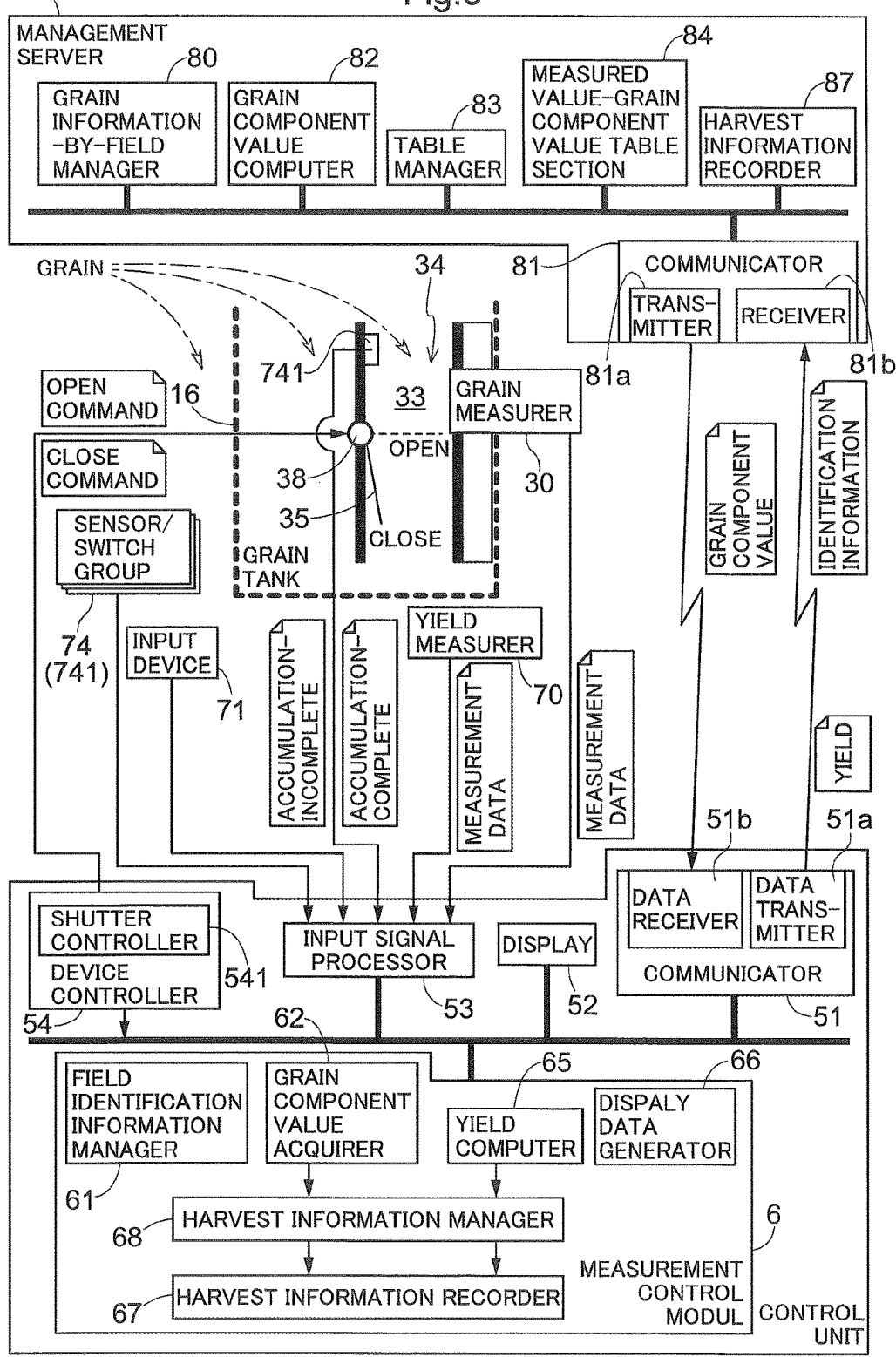
FIG. 8 is a functional block diagram showing one example in which the grain management system is built.

FIG. 8 is a functional block diagram showing a configuration of a grain management system, which is constituted by the above-described combine, and the management server 8 shared between many farmers that own or rent combines, the management server 8 being built in an agricultural management center. Each combine is provided with a measurement control system, which is constituted by the grain measurer 30, the yield measurer 70, and a control unit 5 for building a measurement control module 6. The control unit 5 includes a communicator 51, which is constituted by a data transmitter 51a and a data receiver 51b for exchanging data with the management server 8 via a wireless data communication network, a display 52, which is constituted by a liquid-crystal display panel or the like, an input signal processor 53, which is a data input interface, a device controller 54 for controlling various operation devices, the measurement control module 6, and the like. The functions of the measurement control module 6, which is implemented substantially through the execution of programs, include the functions that are based on the basic principle of the measurement control described using FIG. 1.

Measured value signals from the grain measurer 30 and the yield measurer 70, an accumulation-complete signal (or accumulation-incomplete signal) from the accumulation amount detector 741, which is included in a sensor/switch group 74, input operation signals from input devices 71, such as a touch panel, detection signals from various sensors and switches, and the like are input to the input signal processor 53. Furthermore, signals from switches related to measurement control, such as a measurement start switch (not shown), are also input to the input signal processor 53. The signals input to the input signal processor 53 are subjected to necessary preprocessing, and are transferred to the measurement control module 6. The device controller 54 has a control function for controlling various operation devices installed in the combine. For example, a shutter controller 541 gives an open/close control command to the motor 37 for opening and closing the accumulation shutter 35 in order to temporarily accumulate grains in the grain measurer 30. In this embodiment, a state where a given amount of grain or more has accumulated in the temporary accumulator 33 is detected based on a signal from the accumulation amount detector 741, and then the measurement performed by the grain measurer 30 starts. After the measurement performed by the grain measurer 30 ends, the accumulation shutter 35 is pivoted to the open position, and the grains accumulated in the temporary accumulator 33 are discharged. Next, the accumulation shutter 35 is pivoted to the close position to proceed to the next measurement.

The measurement control module 6 includes a field identification information manager 61, a grain component value acquirer 62, a yield computer 65, a display data generator 66, a harvest information recorder 67, and a harvest information manager 68.

The field identification information manager 61 determines the field in which the combine is to reap culms to harvest grains, and manages the field identification information for specifying the determined field. There are various methods for determining the field subjected to harvest. For example, those methods include: (1) a method in which a field ID is received through short-range wireless communication, or using an OCR, or the like from a field ID holder that is installed in a field, and the field subjected to harvest is determined based on this field ID; (2) a method in which an operator visually checks the actual field while referencing a picture or a map, and inputs the field subjected to harvest through an input device 71 or the like; (3) a method in which, in the case where a correct field map has been created, the field subjected to harvest is determined through matching between the field map and azimuth information (longitude and latitude) obtained by a GPS, and the like.

The grain component value acquirer 62, on the one hand, transmits, to the management server 8, the field identification information managed by the field identification information manager 61 and the measured value related to the grain component value that is the measurement data output from the grain measurer 30. On the other hand, the grain component value acquirer 62 receives the grain component value of harvested grains that is sent from the management server 8.

The yield computer 65 calculates the yield based on the measured value from the yield measurer 70, which is a load cell, using a measured value/yield conversion table. Note that, in this embodiment, the yield computer 65 has a function of calculating the yield per unit of travel distance by calculating the amount of increase in the yield from a designated starting point until a designated end point based on the yield calculated in a given sampling time. The grain component value acquired by the grain component value acquirer 62 and the yield calculated by the yield computer 65 are collected together with the corresponding harvest position (travel position) by the harvest information manager 68, and are recorded in the harvest information recorder 67. The grain component values (moisture and protein) and the yield recorded in the harvest information recorder 67 are converted into visual data by the display data generator 66, and are displayed on the display 52. At this time, the grain component values and the yield can be displayed in units of travel distance, or in units of fields.

The management server 8 includes a grain information-by-field manager 80, the grain component value computer 82, the table manager 83, a measured value-grain component value table section 84, and a harvest information recorder 87, in order to obtain the grain component values based on the field identification information and the measured value related to the grain component that are sent from the combine.

The grain information-by-field manager 80 specifies the field in which the combine is performing harvest work based on the field identification information sent from the combine, and determines the type and breed of harvested grain. For this reason, the grain information-by-field manager 80 has a database from which the type and breed of grain subjected to work are read out, using the field identification information as an extraction condition. Regarding the type and breed of grain, if the type is rice, the breed is Yamato Komachi No. 25 or the like, for example. The table manager 83 determines an optimum measured value-grain component value table for the field subjected to harvest, based on the type and breed of grain, as well as the region, weather conditions of the year, or the like as required, and sets the determined measured value-grain component value table for the measured value-grain component value table section 84. The grain component value computer 82 obtains moisture and protein as grain component values based on the measured value sent from the combine, using the optimum measured value-grain component value table for the field subjected to harvest that is set in the measured value-grain component value table section 84. The grain component values (moisture and protein) calculated by the grain component value computer 82 are transmitted to the combine. Furthermore, these grain component values are also recorded in the harvest information recorder 87 in the management server 8, together with the yield sent from the combine. At this time, the grain component values and the yield can also be recorded so as to be linked with the corresponding harvest position (travel position).

Note that, in this embodiment, the table manager 83 corrects the reference measured value-grain component value table that was prepared in advance, creates the optimum measured value-grain component value table for deriving the grain component values in the field, and sets the determined measured value-grain component value table in the measured value-grain component value table section 84. For example, assuming that S is a component value, X1, X2, . . . each are a spectrometry result group, and F is the reference measured value-grain component value table (measurement line), the reference measured value-grain component value table can be represented as S=F (X1, X2, . . . a1, a2). If coefficient values of a1 and a2 are given by the type and breed of grain, the single, optimum measured value-grain component value table can be determined.

Modifications of First Embodiment

Modifications of the above-described embodiment will be described below. The following modifications are the same as the above-described embodiment except for the content described below. The above-described embodiment and the following modifications may be combined as appropriate, provided there is no inconsistency. Note that the scope of the present invention is not limited to the above-described embodiment and the following modifications.

(1) The classification of the functional units in the functional block diagram shown in FIG. 8 is an example, and those functional units may be arbitrarily integrated or divided. Any configuration may be employed as long as the control functions according to the present invention are realized. Those functions can be realized by hardware and/or software.

(2) In the above-described embodiment, the yield is measured based on an increase in the weight of the grain tank 16. Alternatively, a configuration may be employed in which the yield is also measured using a measurement container for temporarily accumulating a given amount of grain, and the yield per unit of travel (area) is calculated based on the vehicle speed and the time taken until the given amount of grain has accumulated. At this time, an integral structure may be employed in which the measurement unit for yield measurement and the measurement container for grain component measurement are connected to each other, or a separate structure may be employed in which they are separate from each other.

(3) In the above-described embodiment, the communicator 81 in the management server 8 and the communicator 51 in the control unit 5 are directly connected to each other to exchange data. Alternatively, a portable communication terminal, such as a smartphone carried by an operator, may exist between the communicator 81 in the management server 8 and the communicator 51 in the control unit 5. At this time, it is convenient if at least part of the content displayed on the display 52 is also displayed on a display screen of the portable communication terminal.

Second Embodiment

The second embodiment will be described below with reference to FIGS. 9 and 10. Note that, in the following description, constituent elements assigned the same signs as those of the constituent elements in the first embodiment are the same as those in the first embodiment, and a detailed description thereof will be omitted.

Before describing a specific configuration of a combine that serves as the second embodiment of the present invention, a description will be given, using FIG. 9, of a basic configuration of an evaluation system that evaluates grains when the combine harvests the grains. Here, the combine reaps culms in a field using the reaper 14 while traveling, and grains are removed from the reaped culms by a threshing apparatus 15. Grains are supplied from the threshing apparatus 15 to a grain tank 16 by a grain conveyance mechanism. The grain measurer 30 is installed and takes at least some of the grains in the grain supply passage extending from the threshing apparatus 15 to the grain tank 16, and measures grain components. In the case where the crop to be harvested is rice or wheat, the grain components that affect the taste thereof are moisture and protein. For this reason, it is preferable that the grain measurer 30 can output measurement data on moisture and protein. Since this combine can calculate the grain component values when harvesting grains, the operator can check the grain component value during harvest work as a result of a display 152, such as a liquid-crystal display, that is capable of displaying this grain component value being provided.

This combine includes a field identification information manager 161 for managing field identification information for specifying a field. The field identification information manager 161 generates the field identification information for specifying the field in which harvest work is to be performed from now, through manual input of an operator using an input device such as a touch panel, automatic input using a beacon or the like that is installed in the field, matching between a field map and GPS positioning data, or the like. Grain components, such as moisture and protein, are calculated by a grain component value computer 162 based on the measured value from the grain measurer 30. At this time, the grain component value computer 162 uses a function or a table in which the measured value from the grain measurer 30 is an input value, and a specific grain component value is an output value. Here, this function or table (a simple one is also called a measurement line) will be referred to as a measured value-grain component value table, which is for deriving the grain component values from the measured value. The relationship between the measured value and the grain component value differs depending on the type, state, or the like of the grains that are to be measured. Accordingly, in order to obtain an accurate grain component value, an optimum measured value-grain component value table (measurement line) for the grains to be measured needs to be used. A rule or algorithm for generating or selecting such an optimum measured value-grain component value table is considerably complicated. It is also necessary to modify the rule or algorithm using a statistical method whenever necessary. Accordingly, it is not favorable to generate or select an optimum measured value-grain component value table using only a standalone control computer system installed in the combine. For this reason, this combine includes a communicator 151 capable of exchanging data with an external management server 108, which is run on many farms or by farm machine manufacturers. The combine transmits the aforementioned field identification information to a communicator 181 in the management server 108 via a communication line, and receives computation information for the field specified based on this field identification information from the management server 108 via the communicator 181. The table manager 163 determines an optimum measured value-grain component value table using the received computation information. Thus, the grain component value computer 162 can obtain the grain component value based on a measured value using the optimum measured value-grain component value table.

Representative types of computation information that is used by the table manager 163 to determine an optimum measured value-grain component value table are listed below.

(1) A large number of measured value-grain component value tables are prepared in advance in the combine. Selection information for selecting an optimum measured value-grain component value table for the field specified based on the field identification information is set as the computation information. In a simple example, in the case where different measured value-grain component value tables are prepared for each type and/or breed of grain in the combine, the management server 108 uses, as the computation information, the type and/or breed of grain harvested in the field specified based on the field identification information at a current time point. The table manager 163 can use this computation information as a selection condition to select an optimum measured value-grain component value table. This is convenient when the operator of the combine is not familiar with the field or agriculture.

(2) Only a reference measured value-grain component value table to serve as a reference of the measured value-grain component value table is prepared in advance in the combine. Information required for creating an optimum measured value-grain component value table for the field specified based on the field identification information by correcting this reference measured value-grain component value table is set as the computation information. For example, if coefficients of a function for obtaining the grain component value based on the measured value, the tilt of the measurement line, the amount of translation, and the like are used as the computation information, an optimum measured value-grain component value table can be created based on the reference measured value-grain component value table, using this computation information. In a simple example, the coefficients and the tilt may be associated with the type and/or breed of grain, and the type and/or breed of grain may be used as the computation information.

(3) To reduce the burden on the combine to the smallest level, the computation information itself may be configured as an optimum measured value-grain component value table. That is to say, the management server 108 creates, as the computation information, the optimum measured value-grain component value table for the grains harvested in the field specified based on the field identification information, and transmits this to the combine. The table manager 163 need only set the received optimum measured value-grain component value table via a measured value-grain component value table setter 164.

This combine is provided with a temporary accumulation chamber for receiving at least some of the grains supplied to the grain tank 16. The grain measurer 30 may employ an optical measurement apparatus that outputs a measured value based on spectrometry performed on the light with which grains that are temporarily accumulated in the temporary accumulation chamber are irradiated. The grain component value computer 162 can obtain component values of moisture and protein based on this measured value. By repeating, during harvest work, calculation of the grain components while temporarily accumulating harvested grains, grain component values per unit of travel distance, i.e. per minute parcel of the field, can be obtained. A distribution map of each grain component value in a specific field can be created based on this grain component value per minute parcel, which allows accurate farming management to be realized.

Next, a specific embodiment of the combine according to the present invention will be described using the drawings. FIG. 10 is a functional block diagram showing a measurement control system that is built in this combine. This functional block diagram shows the grain measurer 30, the yield measurer 70, and a control unit 105 for building a measurement control module 106, which is a core element of the measurement control system, and the management server 108, which is built in a remote agricultural management center. The control unit 105 includes the communicator 151 capable of performing wireless data communication with the management server 108, the display 152, which is constituted by a liquid-crystal display panel or the like, an input signal processor 153, which is a data input interface, a device controller 154 for controlling various operation devices, the measurement control module 106, and the like. The functions of the measurement control module 106, which is built substantially through the execution of programs, employ the basic principle of the measurement control described using FIG. 9.

Measured value signals from the grain measurer 30 and the yield measurer 70, an accumulation-complete signal (or accumulation-incomplete signal) from the accumulation amount detector 741, which is included in the sensor/switch group 74, input operation signals from input devices 71, such as a touch panel, detection signals from various sensors and switches, and the like are input to the input signal processor 153. Furthermore, signals from switches related to measurement control, such as a measurement start switch (not shown), are also input to the input signal processor 153. The signals input to the input signal processor 153 are subjected to the necessary preprocessing, and are transferred to the measurement control module 106. The device controller 154 has a control function for controlling various operation devices installed in the combine. For example, a shutter controller 641 gives an open/close control command to the motor 37 for opening and closing the accumulation shutter 35 in order to temporarily accumulate grains in the grain measurer 30. In this embodiment, a state where a given amount of grain or more has accumulated in the temporary accumulator 33 is detected based on a signal from the accumulation amount detector 741, and then the measurement performed by the grain measurer 30 starts. After the measurement performed by the grain measurer 30 has ended, the accumulation shutter 35 is pivoted to the open position, and the grains accumulated in the temporary accumulator 33 are discharged. Next, the accumulation shutter 35 is pivoted to the close position to proceed to the next measurement.

The measurement control module 106 includes the field identification information manager 161, the grain component value computer 162, the table manager 163, the measured value-grain component value table setter 164, and a yield computer 165, a display data generator 166, and a harvest information recorder 167, The field identification information manager 161 determines the field in which the combine is to reap culms to harvest grains, and manages the field identification information for specifying the determined field. There are various methods for determining the field subjected to harvest. For example, those methods include: (1) a method in which a field ID is received through short-range wireless communication, or using an OCR, or the like from a field ID holder that is installed in the field, and the field subjected to harvest is determined based on this field ID; (2) a method in which an operator visually checks the actual field while referencing a picture or a map, and inputs the field subjected to harvest through an input device 71 or the like; (3) a method in which, in the case where a correct field map has been created, the field subjected to harvest is determined through matching between the field map and azimuth information (longitude and latitude) obtained by a GPS, and the like.

The yield computer 165 calculates the yield based on the measured value from the yield measurer 70, which is a load cell, using a measured value/yield conversion table. Note that, in this embodiment, the yield computer 165 has a function of calculating the yield per unit of travel distance by calculating the amount of increase in the yield from a designated starting point until a designated end point based on the yield calculated in a given sampling time. The yield calculated by the yield computer 165 is recorded together with the corresponding harvest position (travel position) in the harvest information recorder 167.

The grain component value computer 162 obtains moisture and protein as grain component values based on the measured value from the grain measurer 30, using the optimum measured value-grain component value table for the field subjected to harvest that is set in the measured value-grain component value table setter 164. The optimum measured value-grain component value table for this field subjected to harvest is determined based on the computation information that is sent from the management server 108 as a result of the field identification information managed by the field identification information manager 161 being sent to the management server 108. For this reason, the management server 108 includes a computation information-by-field generator 182. The computation information-by-field generator 182 creates the computation information required for determining an optimum measured value-grain component value table for farm produce (grains) harvested in a field subjected to harvest that is specified based on the field identification information sent through the communicator 151 in the combine and the communicator 181 in the management server 108. The moisture and protein calculated by the grain component value computer 162 are recorded together with the corresponding harvest position (travel position) and the yield calculated by the yield computer 165, in the harvest information recorder 167.

The moisture and protein calculated by the grain component value computer 162, as well as the yield calculated by the yield computer 165 are converted into visual data by the display data generator 166, and are displayed on the display 152. At this time, the grain component values and the yield can be displayed in units of travel distance, or in units of fields.

The table manager 163 sets the optimum measured value-grain component value table used by the grain component value computer 162, for the measured value-grain component value table setter 164. At this time, the table manager 163 determines the optimum measured value-grain component value table using the computation information sent from the computation information-by-field generator 182 in the management server 108. In this embodiment, the computation information-by-field generator 182 extracts, from a database, the type and breed of crop in the field subjected to work, based on the field identification information sent from the combine. The extraction result, e.g. crop attribute data indicating that the type is rice and the breed is Yamato Komachi No. 25, is sent as the computation information to the combine. The table manager 163 corrects the reference measured value-grain component value table, which is prepared in advance, based on the received crop attribute data that serves as the computation information, creates the optimum measured value-grain component value table for deriving the grain component values in the field, and sets the created measured value-grain component value table for the measured value-grain component value table setter 164. For example, assuming that S is a component value, X1, X2, . . . each are a spectrometry result group, and F is the reference measured value-grain component value table (measurement line), the reference measured value-grain component value table can be represented as S=F (X1, X2, . . . a1, a2). If coefficient values of a1 and a2 are given as the computation information, a single, optimum measured value-grain component value table can be determined.

Modifications of Second Embodiment

Modifications of the above-described embodiment will be described below. The following modifications are the same as the above-described embodiment except for the content described below. The above-described embodiment and the following modifications may be combined as appropriate, provided there is no inconsistency. Note that the scope of the present invention is not limited to the above-described embodiment and the following modifications.

(1) Classification of functional units in the measurement control system shown in FIG. 10 is an example, and those functional units may be arbitrarily integrated or divided. Any configuration may be employed as long as the control functions according to the present invention are realized. Those functions can be realized by hardware and/or software.

(2) In the above-described embodiment, the yield is measured based on an increase in the weight of the grain tank 16. Alternatively, a configuration may be employed in which yield measurement is also performed using the measurement container 30A for temporarily accumulating a given amount of grain, and the yield per unit of travel (area) is calculated based on the vehicle speed and the time taken until a given amount of grain has accumulated. At this time, an integral structure may be employed in which the measurement unit 30B for yield measurement and the measurement container 30A for grain component measurement are connected to each other, or a separate structure may be employed in which they are separate from each other.

(3) In the above-described embodiment, the communicator 181 in the management server 108 and the communicator 151 in the control unit 105 are directly connected to each other for data exchange. Alternatively, a portable communication terminal, such as a smartphone carried by an operator, may exist between the communicator 181 in the management server 108 and the communicator 151 in the control unit 105. At this time, it is favorable that at least part of the content displayed on the display 152 is also displayed on a display screen of the portable communication terminal.

INDUSTRIAL APPLICABILITY

The present invention can be used not only for a self-threshing combine, but also a whole culm-feeding type combine. The present invention can also be used not only for a crawler travel-type combine, but also a wheel travel-type combine.

DESCRIPTION OF REFERENCE SIGNS

First Embodiment
14: Reaper
15: Threshing apparatus
16: Grain tank
27: Inlet port
28: Rotary blade
30: Grain measurer
31: Optical probe
32: Housing
33: Temporary accumulator
34: Grain passage
35: Accumulation shutter
5: Control unit
51: Communicator
51a: Data transmitter
51b: Data receiver
52: Display
53: Input signal processor
54: Device controller
6: Measurement control module
61: Field identification information manager
62: Grain component value acquirer
63: Table manager
65: Yield computer
66: Display data generator
67: Harvest information recorder
68: Harvest information manager
70: Yield measurer
71: Input device
8: Management server
80: Grain information-by-field manager
81: Communicator
81a: Transmitter
81b: Receiver
82: Grain component value computer
83: Table manager
84: Measured value-grain component value table section
87: Harvest information recorder
M: internal space
  Second Embodiment
14: Reaper
15: Threshing apparatus
16: Grain tank
30: Grain measurer
33: Temporary accumulator
35: Accumulation shutter
105: Control unit
151: Communicator
152: Display
153: Input signal processor
154: Device controller
106: Measurement control module
161: Field identification information manager
162: Grain component value computer
163: Table manager
164: Measured value-grain component value table setter
165: Yield computer
166: Display data generator
167: Harvest information recorder
70: Yield measurer
71: Input device
108: Management server
181: Communicator
182: Computation information-by-field generator

The invention claimed is:

1. A grain management system comprising:
   a combine for reaping culms in a field while traveling, and accumulating, in a grain tank, grains obtained by threshing reaped culms; and
   a management server for managing quality of the grains harvested by the combine, the combine comprising:
   a grain measurer for outputting a measured value related to a component of the grains supplied to the grain tank; and
   a data transmitter for transmitting the measured value and field identification information for specifying the field to the management server via a communication line, and
   the management server comprising:
   a receiver for receiving the field identification information and the measured value from the combine;
   a table manager for determining a measured value-grain component value table for deriving a grain component value using the measured value based on the field identification information; and
   a grain component value computer for obtaining the grain component value based on the measured value using the measured value-grain component value table that is determined by the table manager.

2. The grain management system according to claim 1,
wherein the management server comprises a field database that records a type of grain, breed of grain, or both, harvested in each field so as to be able to be read out, based on the field identification information, and the table manager determines an optimum measured value-grain component value table based on the type of grain, breed of grain, or both, read out from the field database.

3. The grain management system according to claim 2,
wherein the management server comprises a table storage for storing, in an extractable manner, a plurality of the measured value-grain component value tables associated with a type of harvested grain, breed of harvested grain, or both, and the measured value-grain component value table extracted from the table storage using, as a search condition, a type of grain, breed of grain, or both, read out from the field database is determined as the optimum measured value-grain component value table.

4. The grain management system according to claim 2,
wherein the management server holds a reference measured value-grain component value table to serve as a reference of the measured value-grain component value table, and the table manager determines the optimum measured value-grain component value table by correcting the reference measured value-grain component value table based on the type of grain, breed of grain, or both, read out from the field database.

5. The grain management system according to claim 1,
wherein the management server comprises a transmitter for transmitting, to the combine, the grain component value obtained by the grain component value computer.

6. The grain management system according to claim 5,
wherein the combines comprises:

a second receiver for receiving the grain component value transmitted from the transmitter in the management server; and a display capable of displaying the grain component value.

7. The grain management system according to claim 1,
wherein a temporary accumulation chamber for receiving at least some of the grains supplied to the grain tank is provided, the grain measurer outputs the measured value based on spectrometry performed on light with which the grains temporarily accumulated in the temporary accumulation chamber are irradiated, and the grain component value computer obtains at least a moisture content based on the measured value.

8. The grain management system according to claim 7,
wherein the grain component value computer derives a component value of protein from the measured value.

9. A combine for reaping culms in a field while traveling, and accumulating, in a grain tank, grains obtained by threshing reaped culms, comprising:

a field identification information manager for managing field identification information for specifying the field;

a grain measurer for outputting a measured value related to a component of the grains supplied to the grain tank;

a communicator for transmitting the field identification information to the management server via a communication line, and receiving, from the management server, computation information for the field specified based on the field identification information;

a table manager for determining, using the computation information, an optimum measured value-grain component value table for deriving, from the measured value, a grain component value indicating a component of grains harvested in the field; and a grain component value computer for obtaining the grain component value based on the measured value using the measured value-grain component value table that is determined by the table manager.

10. The combine according to claim 9, further comprising:

a table storage for storing a plurality of the measured value-grain component value tables for deriving the grain component value from the measured value, wherein the table manager determines, as the optimum measured value-grain component value table, the measured value-grain component value table extracted from the table storage using the computation information as a search condition.

11. The combine according to claim 9,
wherein a reference measured value-grain component value table to serve as a reference of the measured value-grain component value table is stored, and the table manager determines the optimum measured value-grain component value table by correcting, based on the computation information, the reference measured value-grain component value table.

12. The combine according to claim 9,
wherein the computation information is a type of grain harvested in the field, breed of grain harvested in the field, or both.

13. The combine according to claim 9,
wherein the computation information is the optimum measured value-grain component value table for deriving the grain component value from the measured value.

14. The combine according to claim 9,
wherein a temporary accumulation chamber for receiving at least some of the grains supplied to the grain tank is provided, the grain measurer outputs the measured value based on spectrometry performed on light with which the grains temporarily accumulated in the temporary accumulation chamber are irradiated, and the grain component value computer obtains at least a moisture content based on the measured value.

15. The combine according to claim 14,
wherein the grain component value computer derives a component value of protein from the measured value.

16. The combine according to claim 9, further comprising:

a display capable of displaying the grain component value.

* * * * *